United States Patent [19]
Hechtenberg et al.

[11] Patent Number: 5,609,607
[45] Date of Patent: Mar. 11, 1997

[54] DEVICE FOR MODELING OR SIMULATING THE SENSE OF TOUCH IN A SURGICAL INSTRUMENT

[75] Inventors: Kurt-Volker Hechtenberg, Bruckmuehl; Dieter Bosch, Munich; Hajo Hermeking, Germering, all of Germany

[73] Assignee: Deutsche Aerospace AG, Munich, Germany

[21] Appl. No.: 313,856

[22] Filed: Sep. 26, 1994

[30] Foreign Application Priority Data

Sep. 24, 1993 [DE] Germany .................. 43 32 580. 7

[51] Int. Cl.$^6$ .................................................. F16K 31/00
[52] U.S. Cl. .................................. 606/205; 251/65
[58] Field of Search ........................ 606/205, 206, 606/207, 208, 209, 210; 251/65; 128/4; 340/407.1, 407.2

[56] References Cited

U.S. PATENT DOCUMENTS

| | | |
|---|---|---|
| 4,535,773 | 8/1985 | Yoon . |
| 4,980,646 | 12/1990 | Zemel . |
| 5,224,954 | 7/1993 | Watts et al. ............... 606/205 |
| 5,269,790 | 12/1993 | Funatsu ............... 606/205 X |
| 5,306,287 | 4/1994 | Becker ............... 606/205 |
| 5,312,420 | 5/1994 | Toso et al. ............... 606/205 X |
| 5,322,258 | 6/1994 | Bosch et al. . |
| 5,337,732 | 8/1994 | Grundfest et al. ............... 128/4 |
| 5,339,799 | 8/1994 | Kami et al. ............... 128/4 |
| 5,451,924 | 9/1995 | Massimino et al. . |

FOREIGN PATENT DOCUMENTS 4213584  11/1992  Germany .

OTHER PUBLICATIONS

"Moderne Aktoren und Sensoren in der Automatisierungstechnik" by Bernd Rech, Published by Universitat des Saarlandes, 28 Sep. 1993.
Sadao Omata and Yoshikazu Terunuma, "New tactile sensor like the human hand and its applications", Mar. 20, 1992, *Sensors and Actuators*, pp. 9 –15.
Kenichiro Suzuki, Khalil Najafi, and Kensall D. Wise, "A 1024–Element High–Performance Silicon Tactile Imager", Aug. 1990, *IEEE Transactions on Electron Devices*, vol. 37, No. 8, pp. 1852 –1860.
Susumu Sugiyama, Ken Kawahata, Masakazu Yoneda, Isemi Igarashi, "Tactile Image Detection Using a 1K–element Silicon Pressure Sensor Array", 1990, *Sensors and Actuators*, pp. 397 –400.
Litian Liu, Xinyu Zheng and Zhiijian Li, "An array tactile sensor with piezoresistive single–crystal silicon diaphragm", 1993, *Sensors and Actuators*, pp. 193–196.
G. J. Monkman, "An Electrorheological Tactile Display", Spring 1992, *Presence*, vol. I, No. 1, The Massachusetts Institute of Technology, pp. 119–228. G. J. Monkman, Robotics Research Unit, Department of Electronic Engineering, University of Hull, Hull, United Kingdom.
Bernd Rech, "Moderne Aktoren und Sensoren in der Saarbrüken," Germany.

*Primary Examiner*—Sam Rimell
*Attorney, Agent, or Firm*—Evenson, McKeown, Edwards & Lenahan, P.L.L.C.

[57] ABSTRACT

Device for modeling or simulating the sense of touch for medical, especially surgical purposes such as operations using medical instruments, characterized in that at least one sensor array which is sensitive to force, pressure, or travel and an actuator array are combined in the instrument to form a "feeling" or "tactile" unit (A, B) in such manner that one controls the other.

30 Claims, 4 Drawing Sheets

Fig.1
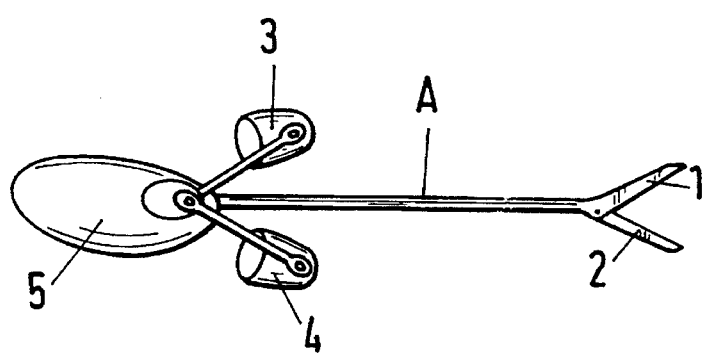
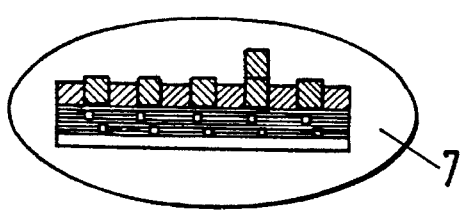
Fig. 1a
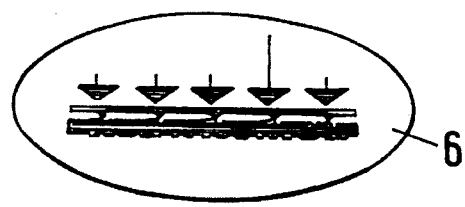
Fig. 1b
Fig.2a
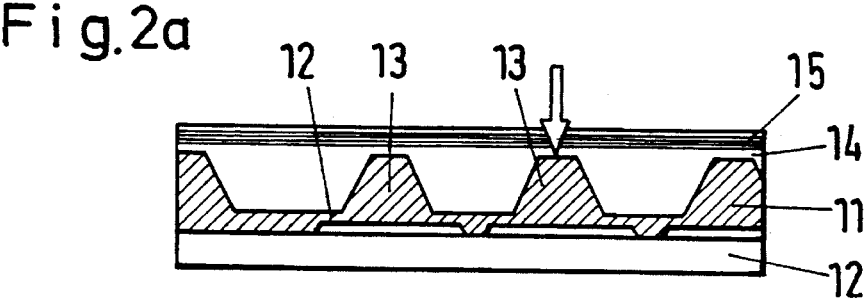
Fig.2b
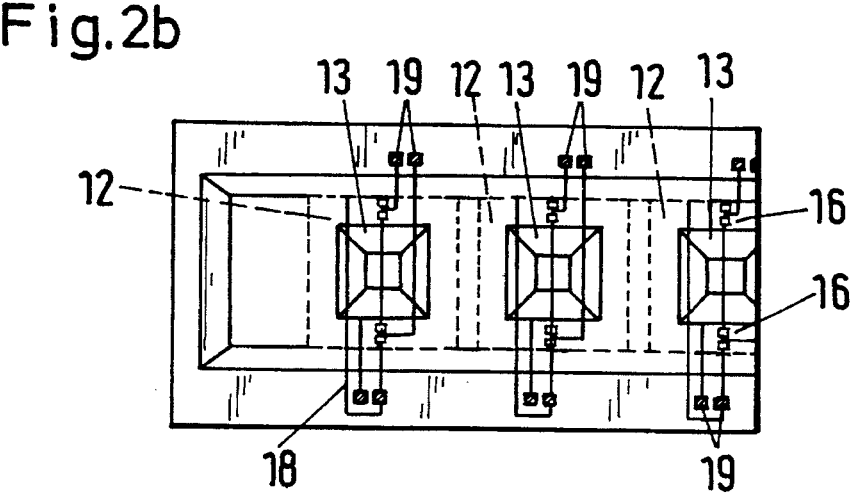

DEVICE FOR MODELING OR SIMULATING THE SENSE OF TOUCH IN A SURGICAL INSTRUMENT

BACKGROUND AND SUMMARY OF THE INVENTION

The invention relates to the further development of certain surgical instruments like those used especially in the area of minimal invasive surgery. These instruments are generally introduced into the interior of the body with the aid of an endoscope and used primarily for diagnostic purposes. One disadvantage of the purely mechanically functioning "tools" of the physician (for example the probe and forceps) is that they do not offer a sense of touch adequate for the surgeon's hand, with whose aid the physician obtains important information during open surgery.

A number of studies are already known with regard to "tactile sensing" which relate mainly to applications in robotics. S. Omata et al., "New tactile sensor like the human hand and its applications," Sensors and Actuators A, 35 (1992) 9.15, describe a tactile sensor based on a piezoelectric oscillator (PZT) to determine the hardness or softness of tissues "quite similarly to the human hand".

K. Suzuki et al., A 1024-Element High-Performance Silicon Tactile Imager," IEEE Trans. El. Dev. 37, 1990, 1852–1860 developed a high-resolution "tactile imager" composed of 1024 (32×32) capacitive pressure sensors for precision robotics.

As the basic component, S. Sugiyama et al., "Tactile Image Detection Using a k-Element Silicon Pressure Sensor Array," Sensors and Actuators A, 2123 (1990), 397–400 describe a pressure sensor array likewise with 32×32 elements.

A device related to the medical field is described in German Patent Document DE-OS 42 13 584. In this so-called "object information modeling device" (diagnostic device) in the first embodiment which is relevant here, an endoscope device is described for optical (i.e. zero contact) object acquisition. By means of stereo CCD optics, the data for generating a 3 D image on a monitor are collected. This height profile can be selected pointwise with a mouse. An actuator integrated into the mouse, in the form of a bending rod (driven by piezo or SMA elements) is adjusted as a function of the relative height of the object point and can be felt with the finger. Hence the diagnosis is limited to pure modeling of "unevenness" or "degree of swelling" of the object under investigation. Of course its elastic properties (hardness) cannot be determined. In another embodiment of German Patent Document DE-OS 42 13 584, detection of object temperature using IR sensing is proposed as well.

In the present invention, an actuator array made of so-called "ERF cells" is used as the key element for the desired modeling of the sense of touch. These are control elements that contain an electrorheologic fluid (ERF) as an active medium.

ERF actuators have been described in the past in the form of couplings, shock absorbers (active damping system), valves, and pumps.

In contrast to the highly complex diagnostic system described in German Patent Document DE 42 13 584 A1, the goal of the present invention is to implement the functions of (i) detection of object properties that can be determined by feel, and (ii) direct modeling of these properties in a manner that can be felt, within a single endoscopic instrument. This instrument can be desinged either as a so-called probe or as forceps.

Other objects, advantages and novel features of the present invention will become apparent from the following detailed description of the invention when considered in conjunction with the accompanying drawings.

BRIEF DESCRIPTION OF THE DRAWINGS

FIG. 1 is a schematic diagram of a forceps constructed according to a preferred embodiment of the invention;

FIG. 1a is an enlarged schematic view of an actuator array arranged in section X of FIG. 1;

FIG. 1b is an enlarged schematic view of a sensor array arranged in section Y of FIG. 1;

FIG. 2a is a cross sectional view of a pressure sensor array in a silicon-micromechanical design, constructed according to a preferred embodiment of the invention, and usable as the schematically depicted sensor array of FIG. 1b;

FIG. 2b is a top schematic view of the array of FIG. 2a;

FIG. 3 is an enlarged schematic view which shows an ERF cell element, which is used for modeling the sense of touch in the sensor array of FIG. 1a;

FIG. 4b is a top view of the array of FIG. 4a;

FIG. 7a is a schematic pictorial view of a probe that can be substituted for the forceps in the endoscopic application shown in FIG. 7 according to another embodiment of the invention.

DETAILED DESCRIPTION OF THE PREFERRED EMBODIMENTS

Figure 3:
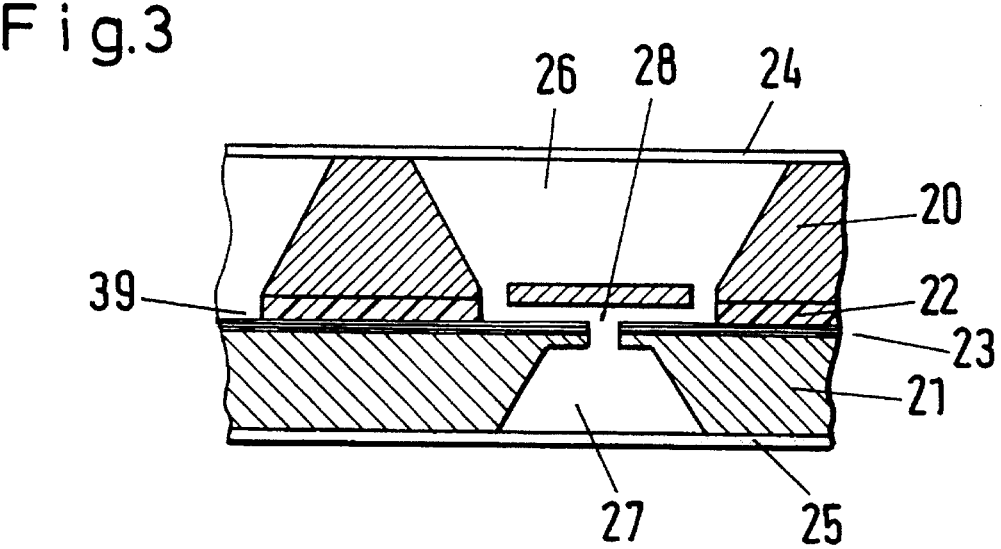

FIG. 1 is a schematic diagram of a forceps assembly constructed according to a preferred embodiment of the invention. On the inner surface of the two forceps jaws 1 and 2 (or, optionally, of only one jaw) sensor arrays 6 (FIG. 1b) sensitive to force and pressure are located. The sensor arrays 6 supply analog electrical signals to a display D (see FIG. 7) when objects are touched and gripped. The signal generated by each sensor element in array 6 corresponds to the respective local soft or hard consistency of the tissue grasped. With the aid of the sensor signals, this tissue structure is modeled/simulated in actuator array 7 (FIG. 1a), located in the correspondingly designed grips 3, 4 of the forceps. surface of this array is felt with the fingertip(s). In this manner, the grip and feel of organs inside the body are conveyed to the outside. The important elements of a probe B (FIGS. 5 and 7), or forceps A (FIG. 1) for feeling tissue structure C beneath an abdominal wall G according to FIGS. 1 and 7 will now be described in further detail.

FIGS. 2a and 2b show, in cross section in FIG. 2a and in a top view in FIG. 2b, a pressure sensor array in a silicon-micromechanical design. Central silicon element 11 is so designed, especially etched, that depending on the desired local resolution, a plurality of n individual sensor elements is formed at specified lateral intervals. Each element consists of a membrane, especially a square membrane 12 with a closed ring configuration, each of which has at the center a sensing body 13 in the shape of a pyramid with a flat top. The area etched away between these sensing bodies is filled with a highly elastic silicone material 14. This material is sealed off from the exterior by a thin fabric-reinforced membrane 15 and protected against damage. The forces acting from the outside are mainly transferred by sensing bodies 13 to membrane 12. The deflection of sensing bodies 13 is converted into corresponding electrical signals in manner usual for piezoresistive pressure sensors with piezoresistance bridges. A ceramic substrate 17 serves as a support for electrical leads 18 and contact surfaces 19.

The ERF cell shown in FIG. 3 consists mainly of two microstructured Si parts 20 and 21, a glass intermediate layer 22, an Al electrode 23 and two thin flexible membranes 24 and 25. These membranes close off two chambers 26 and 27 on both sides, said chambers being filled with an electrorheological fluid. In this diagram, 26 is a pressure chamber and 27 is a pressure compensating chamber.

The ERF cell functions as follows:

If upper membrane 24 is moved downward by an external force, fluid is expelled from pressure chamber 16 into compensating chamber 27. It must pass through a throttle channel 28 within which the flow resistance can be varied within wide limits by an electrical field (electrotheological effect). The electrical field is generated by applying a voltage between electrode 23 and upper Si part 20. The external force, which results for example from finger pressure, encounters an opposite force that increases or decreases as the field is varied (the ERF is nearly incompressible), and accordingly the material in pressure chamber is perceived as being more or less soft or hard. The feeling process is reversible in that, with the aid of lower membrane 25, a restoring force is generated that serves to equalize the pressure when the field is shut off.

As in the case of the physiological sense of touch, its simulation by the ERF cell is a dynamic process, i.e. the information ("hard" or "soft") is transmitted only when the sensing element is moving or when the force is changed.

Figure 4A:
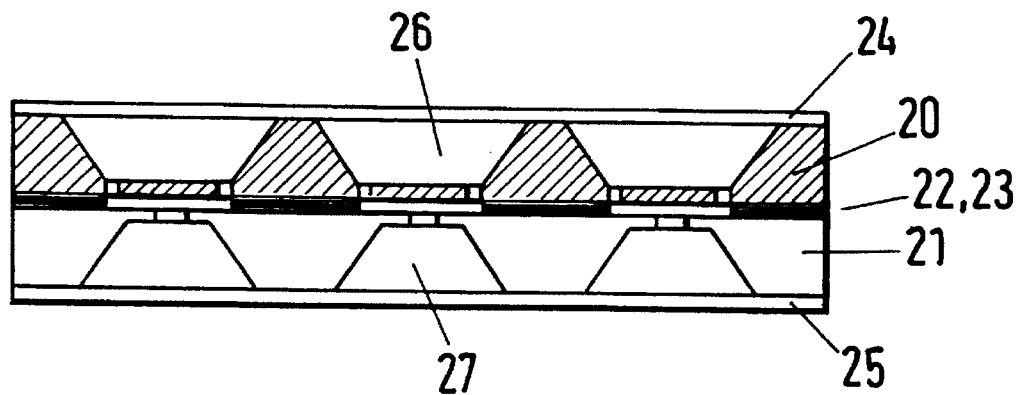
FIG. 4a is a schematic sectional view of an ERF actuator array composed of a row of individual elements.
Figure 4B:
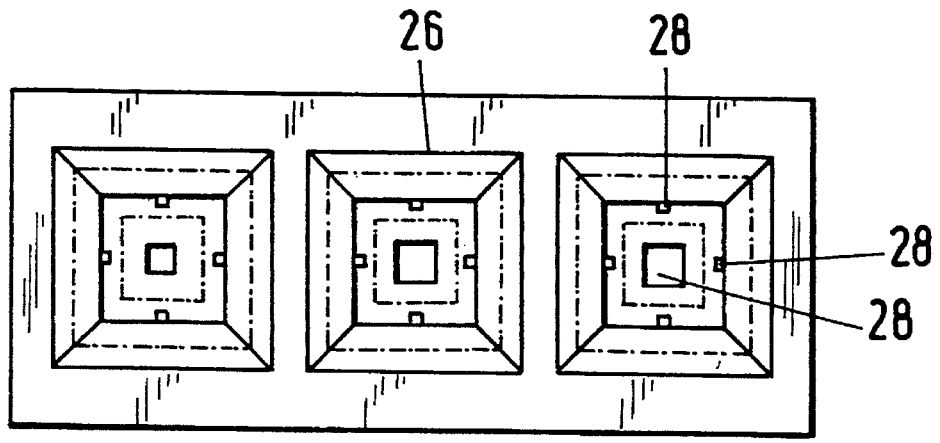

FIGS. 4a and 4b show an ERF actuator array composed of a row of individual elements, in section in FIG. 4a and in a top view in FIG. 4b. In the top view of FIG. 4b, the positions of the throttle connecting channels 28 between pressure chamber 26 and compensating chamber 27 can be seen.

Figure 5:
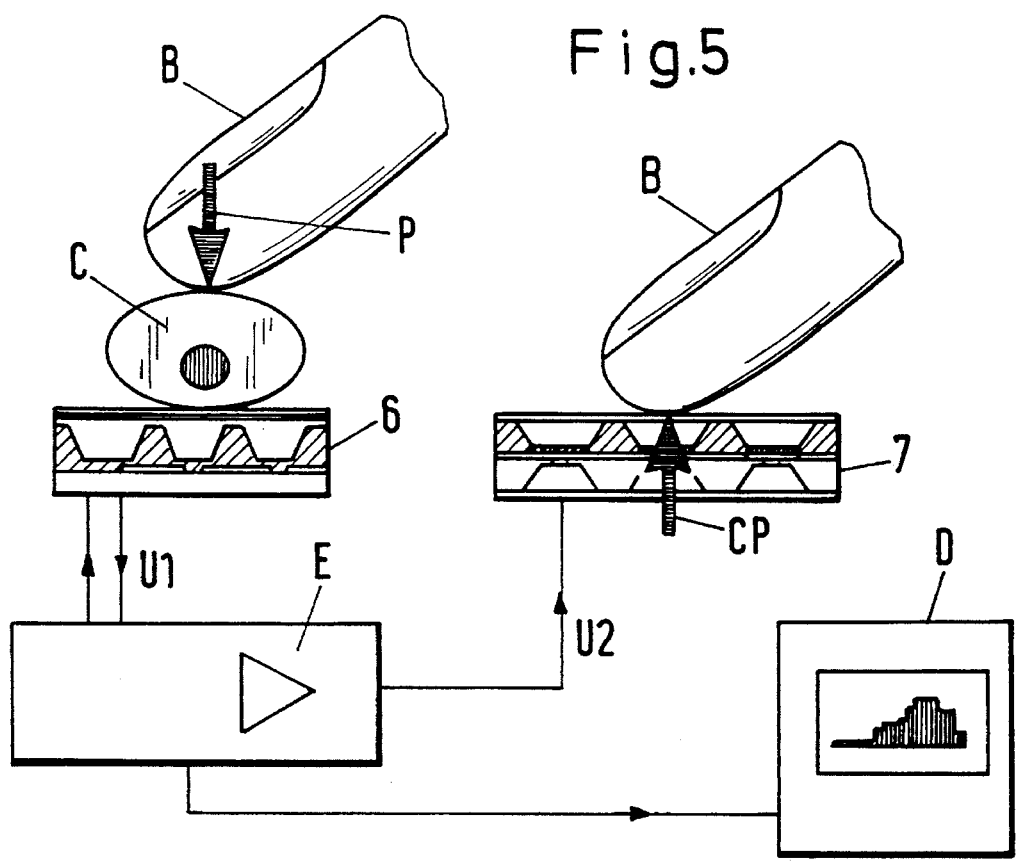
FIG. 5 is a schematic diagram of the function of the combined sensor and actuator components according to the invention.

The function according to the invention of the combined sensor and actuator components described above is shown in FIG. 5. The figure shows a test object C resting on a pressure sensor array, on which finger B exerts a vertical sensing force (FIG. 5, upper left). The sensor signal U1 corresponding to this force is used directly to generate a proportional actuator operating voltage U2. If finger B presses simultaneously on the surface of actuator array 7, in the ideal case it feels a reaction force identical to the vertical sensing force (at the bottom right in FIG. 2). By adjustment (amplification with GCA Gain Control Anplifier) of the transmission factor of the electronics and calibration of signal processing unit E for different materials, the quality of modeling of the sensed information can be improved in stages, as in a microcomputer or microprocessor operating as a neuronal network.

Direct imaging of the pressure/force profile on a video display D for example can be accomplished in known fashion and is an integral component of the entire system.

FIG 6, 6a–6d graphically depict in a simplified manner the function of the system, especially the correlation between the sensor and the actuator. A "normal sensing pulse, T" set with respect to feeling force, with a constant penetration depth, in soft and hard tissue or a similar medium to be felt, generates sensor signals P of different heights in a sensor array 6. These in turn are utilized electronically as mentioned above (at E) to generate actuator control voltages U of different kinds, which in the corresponding ERF cell produce the proportional changes in viscosity N of the electrorheological fluid ERF in throttle channel 28. When feeling the surface of each cell (FIG. 3) of array 7, one feels the counter pressure CP of various heights shown in the actuator membrane.

Figure 7:
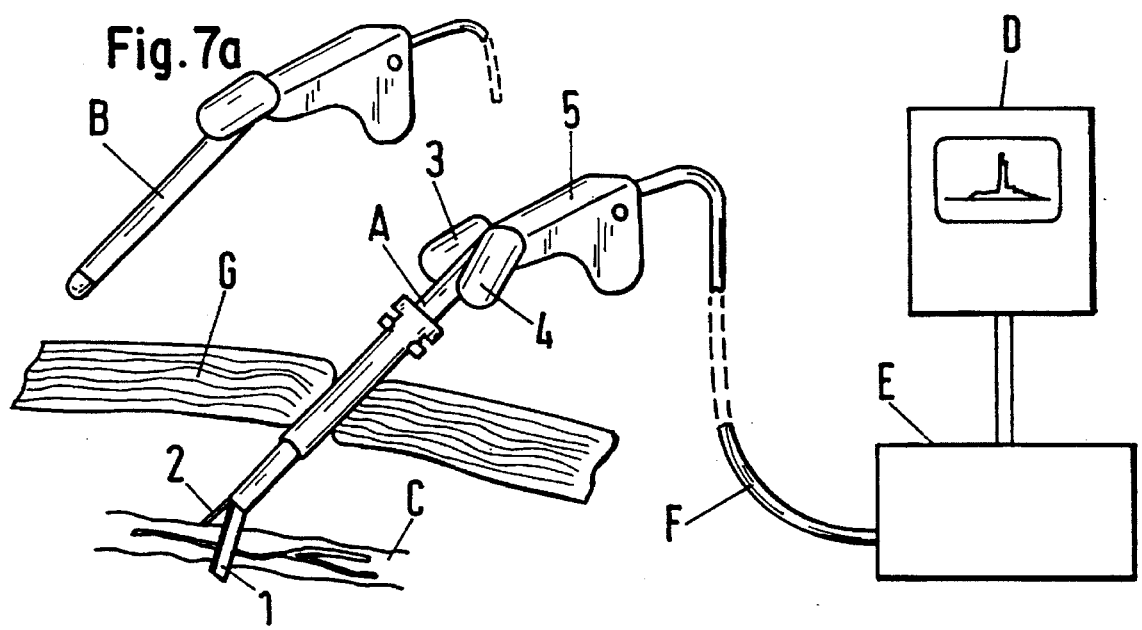
FIG. 7 is a schematic pictorial view which shows forceps according to the invention in a typical endoscopic application.
Figure 6:
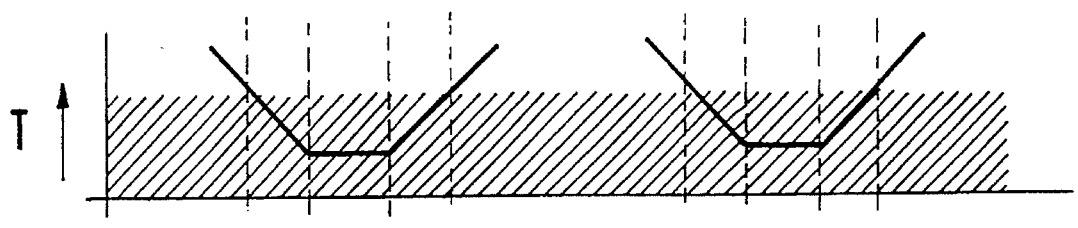
FIG. 6, 6a–6d are a graphical representation which serves to clarify the function of the system described, showing signal processing, especially the correlation between the sensor and actuator from top to bottom.
Figure 6A:
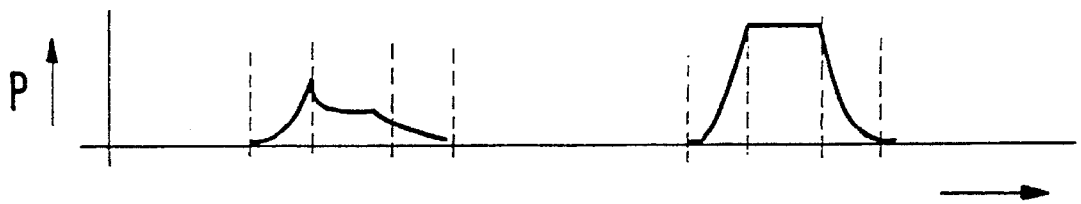
Figure 6B:
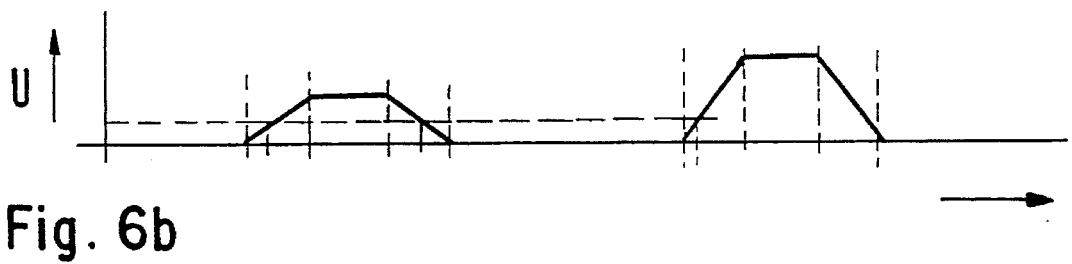
Figure 6C:
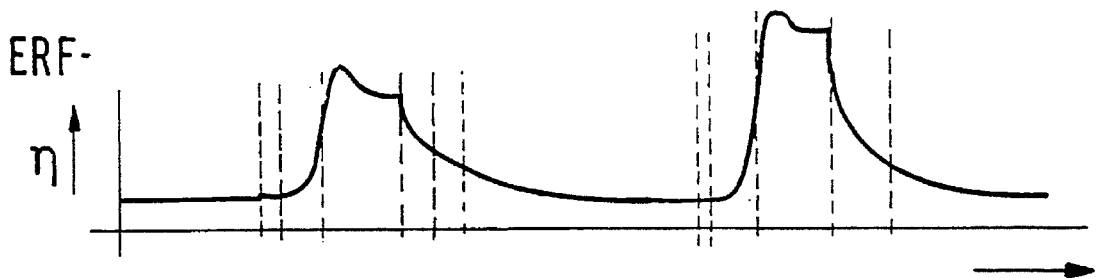
Figure 6D:
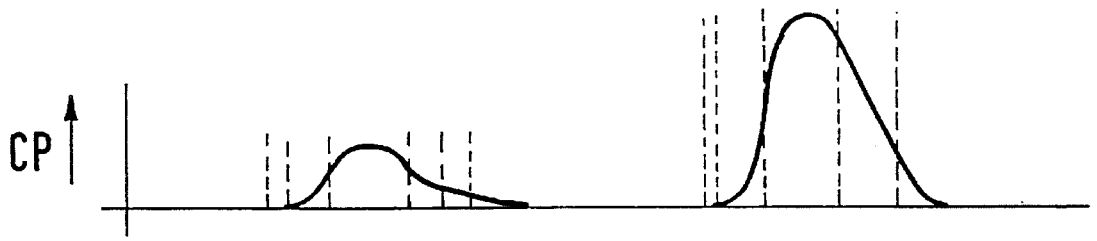

Finally, FIG. 7 shows forceps A according to the invention as well as probe B, designed and functioning completely analogously, in a typical endoscopic application. A body organ C is gripped as an object by forceps jaws 1 and 2. The pressure distribution thus produced on sensor array 6 is displayed on display D and also used to simulate the sense of touch (see FIGS. 6, 6a–6d), in finger grips 3, 4. The instrument is guided by means of grip 5, which simultaneously serves as a housing for supply lead F and electronics E. The electronic control and computer unit has the following functions:

Generation of sensor measurement data for visual display in D;

Function monitoring and generation of optical and/or acoustic warning signals in D;

Performance of self-testing and calibration operations;

Storage (in RAM, ROM, EPROM) of individual diagnostic data, especially when the handle of forceps A serves as an endoscope.

Another design of the invention provides for replacing the control and signal lead F between forceps A and unit E by a telemetric transmission line, not shown, as is already the prior art in many cases. This means a considerable improvement with regard to the ease of use of the instruments described.

Other modifications of the embodiments described and combinations for the same purpose with means known of themselves, such as other sensors (for temperature, current, etc.), can readily be made by the individual skilled in the art. The same is true for programming any microcomputers (MC) or microprocessors (MP) used for the purpose as well as their software, if a MC of the self-learning design (neuronal network) is not used.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A surgical instrument for treating tissue, comprising:

a tissue contacting member, a manually engageable handle operatively connected to the tissue contacting member, a sensor array on said tissue contacting member, an actuator array on said handle, and an electric signal circuit connecting the sensor array and the actuator array, wherein the actuator array is formed by a plurality of pressure sensitive cells containing electrorheological fluid.

2. An instrument according to claim 1, wherein said tissue contacting member is a probe member.

3. An instrument according to claim 1, wherein said tissue contacting member is part of a forceps.

4. An instrument according to claim 1, wherein each of said pressure sensitive cells comprises a pressure chamber and a pressure compensating chamber, the pressure chamber communicating with the pressure compensating chamber via at least one throttle channel.

5. An instrument according to claim 4, wherein the pressure chamber is formed in a first part and is bounded by a first membrane, and the pressure compensating chamber is formed in a second part and is bounded by a second membrane.

6. An instrument according to claim 5, wherein an intermediate layer and an electrode are disposed between the first part and the second part.

7. An instrument according to claim 6, wherein said electric signal circuit produces a voltage corresponding to a pressure applied to said sensor array, said voltage being applied between the electrode and the first part to control a flow resistance of the electrorheological fluid through the at least one throttle channel.

8. An instrument according to claim 1, wherein the sensor array is formed by a plurality of sensing elements.

9. An instrument according to claim 8, wherein each of the sensing elements comprises a membrane having a sensing body, the sensing bodies of adjacent of the sensing elements being laterally separated by spaces.

10. An instrument according to claim 9, wherein the spaces are filled with an elastic material.

11. An instrument according to claim 10, wherein the elastic material is sealed off opposite the membrane by another membrane.

12. An instrument according to claim 1, wherein the electric signal circuit includes an electronic control unit which converts electric signals from the sensor array to electric signals for the actuator array.

13. An instrument according to claim 12, wherein the electronic control unit performs self-testing functions.

14. An instrument according to claim 12, wherein the electronic control unit converts electric signals from the sensor array to sensor data for visual display, and wherein a visual display unit is connected to the electronic control unit which visually displays the sensor data.

15. An instrument according to claim 12, wherein the electronic control unit generates a warning signal when an error occurs in the conversion of the electric signals, said warning signal being visually or acoustically transmitted.

16. An instrument according to claim 1, wherein the electric signal circuit comprises a telemetric transmission line.

17. An instrument for simulating a sense of touch of an object, comprising:
   a contacting member for engagement with the object,
   a sensor array arranged on said contacting member to sense a contact pressure,
   a manually engageable surface operatively connected to the contacting member,
   an actuator array arranged on the manually engageable surface, and
   an electric signal circuit connecting the sensor array and the actuator array, wherein the actuator array comprises a plurality of pressure sensitive cells containing electrorheological fluid, said actuator array transmitting a pressure which corresponds to the contact pressure to the manually engageable surface.

18. An instrument according to claim 17, wherein each of said pressure sensitive cells comprises a pressure chamber and a pressure compensating chamber, the pressure chamber communicating with the pressure compensating chamber via at least one throttle channel.

19. An instrument according to claim 18, wherein the pressure chamber is formed in a first part and is bounded by a first membrane, and the pressure compensating chamber is formed in a second part and is bounded by a second membrane.

20. An instrument according to claim 19, wherein an intermediate layer and an electrode are disposed between the first part and the second part.

21. An instrument according to claim 20, wherein said electric signal circuit produces a voltage corresponding to said contact pressure, said voltage being applied between the electrode and the first part to control a flow resistance of the electrorheological fluid through the at least one throttle channel.

22. An instrument according to claim 17, wherein the sensor array is formed by a plurality of sensing elements.

23. An instrument according to claim 22, wherein each of the sensing elements comprises a membrane having a sensing body, the sensing bodies of adjacent of the sensing elements being laterally separated by spaces.

24. An instrument according to claim 23, wherein the spaces are filled with an elastic material.

25. An instrument according to claim 24, wherein the elastic material is sealed off opposite the membrane by another membrane.

26. An instrument according to claim 17, wherein the electric signal circuit includes an electronic control unit which converts electric signals from the sensor array to electric signals for the actuator array.

27. An instrument according to claim 26, wherein the electronic control unit performs self-testing functions.

28. An instrument according to claim 26, wherein the electronic control unit converts electric signals from the sensor array to sensor data for visual display, and wherein a visual display unit is connected to the electronic control unit which visually displays the sensor data.

29. An instrument according to claim 26, wherein the electronic control unit generates a warning signal when an error occurs in the conversion of the electric signals, said warning signal being visually or acoustically transmitted.

30. An instrument according to claim 17, wherein the electric signal circuit comprises a telemetric transmission line.

* * * * *